United States Patent [19]

Cummings

[11] Patent Number: 5,298,501

[45] Date of Patent: Mar. 29, 1994

[54] CHEMICALLY STABLE GRANULES CONTAINING INSECTICIDAL PHOSPHOROAMIDOTHIOATES

[75] Inventor: Gary Cummings, Moraga, Calif.

[73] Assignee: Valent U.S.A. Corporation, Walnut Creek, Calif.

[21] Appl. No.: 15,673

[22] Filed: Feb. 9, 1993

Related U.S. Application Data

[63] Continuation of Ser. No. 674,857, Mar. 25, 1991, abandoned.

[51] Int. Cl.$^5$ .............................................. A01N 57/12
[52] U.S. Cl. .................................. 514/120; 424/710; 514/137
[58] Field of Search ................ 424/710; 514/973, 119, 514/120

[56] References Cited

U.S. PATENT DOCUMENTS

| | | | |
|---|---|---|---|
| 378,583 | 2/1888 | Feustell | 424/710 |
| 3,585,022 | 6/1971 | Gray | 71/65 |
| 3,622,677 | 11/1971 | Short | 424/361 |
| 3,716,600 | 2/1973 | Magee | 260/959 |
| 3,845,172 | 10/1974 | Magee | 424/219 |
| 3,914,417 | 10/1975 | Magee | 424/219 |
| 3,919,416 | 11/1975 | Cosby | 424/162 |
| 5,075,058 | 12/1991 | Chan et al. | 264/118 |
| 5,100,667 | 3/1992 | Chan et al. | 424/405 |

FOREIGN PATENT DOCUMENTS

0415609A2 3/1991 European Pat. Off. .
WO/91/111-
04 8/1991 PCT Int'l Appl. .

*Primary Examiner*—Richard L. Raymond
*Assistant Examiner*—Brian M. Burn
*Attorney, Agent, or Firm*—Sughrue, Mion, Zinn, Macpeak & Seas

[57] ABSTRACT

Chemically stable granular insecticidal compositions of phosphoroamidothioates and phosphoroamidodithioates are provided. These compositions comprise at least 83 weight percent of ammonium sulfate effective for granulating the insecticidal components. Insecticidal methods employing these granules are also disclosed.

20 Claims, No Drawings

CHEMICALLY STABLE GRANULES CONTAINING INSECTICIDAL PHOSPHOROAMIDOTHIOATES

This is a continuation of application No. 07/674,857 filed Mar. 25, 1991 (now abandoned).

BACKGROUND OF THE INVENTION

1. Field of the Invention

The present invention is directed to granular compositions containing insecticidal phosphoroamidothioates as well as to methods for employing said compositions. In particular, the present invention is directed to chemically stable granules of insecticidal phosphoroamidothioates which granules contain a sufficient amount of ammonium sulfate so as to impart chemical stability to the phosphoroamidothioates as well as to methods for killing insects which utilize such compositions.

2. State of the Art

Insecticidal compositions in various forms are available for rather diverse methods of application. The method of preparation of the insecticidal composition is largely determined by the physical and chemical nature of the insecticide and the intended use and method of application of the insecticide to the area to be treated.

Certain phosphoroamidothioates and phosphoroamidodithioates are known in the art as having excellent insecticidal activity against a variety of insects and in a variety of environments. A particularly important commercial insecticide within these classes of compounds is the insecticide acephate (generic name) or Orthene ® (tradename) which can be systemically taken up by a plant so that insects which feed and/or live on the plant are killed, in addition to those insects which directly ingest or are contacted by the insecticide. Acephate and related compounds are described in U.S. Pat. Nos. 3,716,600, 3,845,172 and 3,914,417, which references disclose that in addition to their insecticidal properties, the compounds disclosed therein possess very low mammalian toxicity. Orthene ® is commercially produced as a technical grade chemical of about 97 to 99.5% purity.

One method of formulating technical grade phosphoroamidothioates for commercial use is to mix the technical grade powder with an anti-caking agent, such as fumed silica, and a wetting agent. The wetting agent is utilized to wet the insecticide and the anti-caking agent is used to prevent agglomeration of the insecticide in its container. This formulation of insecticide can be applied to crops as a spray solution or as a dust.

Use of phosphoroamidothioates as powders allows for relatively high concentrations of insecticide to be applied to a treatment area, but the powder application suffers from various disadvantages. First, the finely divided particles of active spray may be carried by air currents into areas where harmful effects may occur. In addition, it is difficult to apply sprays or dusts to the soil surface or to lower areas of plants when dense foliage must be penetrated. Finally, powdered phosphoroamidothioates suffer from chemical stability problems due to hydrolytic and catalytic driven degradation which shortens the shelf life of the powdered insecticide.

While the use of granules or pellets would overcome some of the inherent difficulties involved in using sprays or dusts, granular formulations of insecticidal phosphoroamidothioates still suffer chemical stability problems which interfere with the commercial feasibility of such formulations.

In the present invention, it has been found that granules of insecticidal phosphoroamidothioates containing a sufficient amount of ammonium sulfate possess improved chemical stability as compared to similar granules containing less ammonium sulfate. Specifically, in the present invention, granules of insecticidal phosphoroamidothioates containing at least about 83 weight percent of ammonium sulfate possess improved chemical stability as compared to granules containing less than 83 weight percent ammonium sulfate.

While the use of ammonium sulfate with phosphoroamidothioates in pellets has been heretofore suggested, the use of at least 83 weight percent ammonium sulfate has not been suggested nor has it been suggested that the use of such amounts would impart improved chemical stability to granules containing insecticidal phosphoroamidothioates as compared to use of less than 83 weight percent.

Likewise, while U.S. Pat. No. 3,585,022, discloses granules containing a pesticide and from 30 to 90 parts by weight of crystalline salt, this reference fails to teach the use of ammonium sulfate or granules of ammonium sulfate in combination with insecticidal phosphoroamidothioates. Moreover, this reference fails to disclose that use of a sufficient amount of ammonium sulfate will impart chemical stability to the phosphoroamidothioates.

SUMMARY OF THE INVENTION

The present invention is directed to the discovery that granules of insecticidal phosphoroamidothioates containing a sufficient amount of ammonium sulfate possess superior chemical stability as compared to granules containing less ammonium sulfate.

Accordingly, in one of its composition aspects, the present invention is directed to a granular insecticidal composition comprising at least about 2 weight percent of an insecticidal compound or mixture of compounds of the formula:

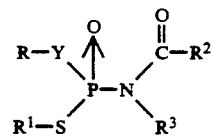

where R and $R^1$ individually are alkyl, alkenyl or alkynyl containing up to 6 carbons, $R^2$ is hydrogen, alkyl containing 1 to 18 carbon atoms, cycloalkyl containing 3 to 8 carbon atoms, alkenyl containing 2 to 18 carbon atoms or alkynyl containing 3 to 18 carbon atoms, $R^3$ is hydrogen or alkyl containing 1 to 6 carbon atoms, and Y is oxygen or sulfur;

and at least about 83 weight percent of ammonium sulfate.

In another of its composition aspects, the present invention is directed to a granular insecticidal composition comprising about 2 to about 17 weight percent of an insecticidal compound or mixture of compounds of the formula:

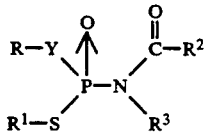

where R and $R^1$ individually are alkyl, alkenyl or alkynyl containing up to 6 carbons, $R^2$ is hydrogen, alkyl containing 1 to 18 carbon atoms, cycloalkyl containing 3 to 8 carbon atoms, alkenyl containing 2 to 18 carbon atoms or alkynyl containing 3 to 18 carbon atoms, $R^3$ is hydrogen or alkyl containing 1 to 6 carbon atoms, and Y is oxygen or sulfur;

and about 83 to about 98 weight percent ammonium sulfate.

In one of its method aspects, the present invention is directed to a method for killing insects which comprises contacting insects or their growth habitats with an insecticidally effective amount of granules comprising at least about 2 weight percent of a compound of the formula:

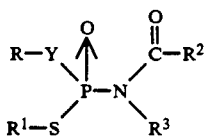

where R and $R^1$ individually are alkyl, alkenyl or alkynyl containing up to 6 carbons, $R^2$ is hydrogen, alkyl containing 1 to 18 carbon atoms, cycloalkyl containing 3 to 8 carbon atoms, alkenyl containing 2 to 18 carbon atoms or alkynyl containing 3 to 18 carbon atoms, $R^3$ is hydrogen or alkyl containing 1 to 6 carbon atoms, and Y is oxygen or sulfur;

and at least 83 weight percent of ammonium sulfate.

In another of its method aspects, the present invention is directed to a method for killing insects which employs the ability of phosphoroamidothioates to be systemically absorbed by plants and when so absorbed, insects ingesting said plants will be killed. This method comprises contacting plants which are ingested by said insects or the plant's growth medium with a granular composition comprising at least about 2 weight percent of a compound of the formula:

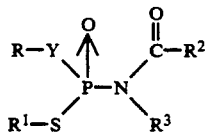

where R and $R^1$ individually are alkyl, alkenyl or alkynyl containing up to 6 carbons, $R^2$ is hydrogen, alkyl containing 1 to 18 carbon atoms, cycloalkyl containing 3 to 8 carbon atoms, alkenyl containing 2 to 18 carbon atoms or alkynyl containing 3 to 18 carbon atoms, $R^3$ is hydrogen or alkyl containing 1 to 6 carbon atoms, and Y is oxygen or sulfur;

and at least 83 weight percent of ammonium sulfate.

DETAILED DESCRIPTION OF THE PREFERRED EMBODIMENTS

The present invention is directed to the discovery that granular insecticidal compositions of phosphoroamidothioates and related insecticidal compounds possess unexpected and superior chemical stability when these granules contain at least about 83 weight percent ammonium sulfate. Additionally, it has also been unexpectedly discovered that the use of the same level of compounds related to ammonium sulfate do not impart similar chemical stability to the granular formulation.

As used herein, the term "granules" refer to solid pellets, granules, grains and the like. Such granules can include those wherein the phosphoroamidothioates comprise the core of the granule and the ammonium sulfate forms a coating over the core; those wherein the ammonium sulfate comprises the core of the granule and the phosphoroamidothioates forms a coating over the core; and those wherein there is no discreet core or coatings (i.e., a granule having a substantially uniform composition throughout).

The active insecticidal component in the granular formulation of this invention is a compound or mixture of compounds of the formula:

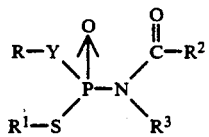

where R and $R^1$ individually are alkyl, alkenyl or alkynyl containing up to 6 carbons, $R^2$ is hydrogen, alkyl containing 1 to 18 carbon atoms, cycloalkyl containing 3 to 8 carbon atoms, alkenyl containing 2 to 18 carbon atoms or alkynyl containing 3 to 18 carbon atoms, $R^3$ is hydrogen or alkylcontaining 1 to 6 carbon atoms, and Y is oxygen or sulfur.

Particularly preferred compounds are those in which R and $R^1$ are independently methyl, ethyl, allyl or alkenyl; $R^2$ is H or alkyl; $R^3$ is hydrogen; and Y is oxygen. The most preferred compound is that in which R, $R^1$, and $R^2$ are methyl, $R^3$ is hydrogen and Y is oxygen. Compounds of the above formula may be prepared as described in U.S. Pat. Nos. 3,716,600, 3,845,172 and 3,914,417, which are incorporated herein by reference in their entirety. Likewise, acephate (R, $R^1$, $R^2$ are $CH_3$; $R^3$ is hydrogen and Y is oxygen) is commercially available from Chevron Chemical Company, San Ramon, Calif. [e.g., Orthene® 90S (90% acephate), Orthen® 80S (80% acephate) and Orthene® 75S (75% acephate)].

The insecticidal component is generally present in the granule in an amount of from at least 2 weight percent. Preferably, the insecticidal component will be present in an amount of about 2 to about 17 weight percent, even more preferably, the insecticidal component will be present in an amount of from about 8 to about 15 weight percent and, most preferably, the insecticidal component will be present in about 15 weight percent.

The granular formulation of this invention is prepared by admixing the requisite amount of an insecticidal phosphoroamidothioate or a mixture of insecticidal phosphoroamidothioates with at least about 83 weight percent ammonium sulfate. Preferably, the ammonium sulfate will be present in an amount of from about 83 to about 98 weight percent, even more preferably, the ammonium sulfate will be present in an amount of from about 85 to about 92 weight percent and, most preferably, the ammonium sulfate will be present in about 85 weight percent.

One or more optional additives can be included in this admixture including colloidal silica particles, such as Cab-O-Sil TM, corn starch, magnesium stearate, surfactants and deodorants. The colloidal silica particles and magnesium stearate are used as processing aids and are generally employed in amounts of from about 0.5 to about 5 weight percent of the granular composition.

Corn starch is employed as a binding agent to make the granule harder. However, insofar as compositions of this invention which do not contain binding agent are sufficiently hard, the presence of such binding agents is not necessary. However, when a binding agent is employed, it is generally employed in amounts of from about 1 to about 8 weight percent of the granular composition.

Surfactants can be employed to add or retard granule disintegration after application. When employed, the surfactants will generally comprise from about 0.2 to about 5 weight percent of the granular composition.

Deodorants (as well as reodorants) can be used to mask the acephate odor. When employed, the deodorants and reodorants will generally comprise from about 0.05 to about 2 weight percent of the granular composition.

In addition to the above-recited optional ingredients, the granules of this invention can optionally contain one or more active ingredients in combination with the phosphoroamidothioate(s). Such active ingredients include, for example, fungicides, and are employed in amounts effective for their intended purpose (e.g., a fungicidally effective amount).

The complete admixture is then processed into granules. For example, the granules can be made by compaction of the complete admixture. Specifically, the complete admixture is generally mixed to uniformity, ground through a hammer mill (e.g., a Fitz hammer mill), compressed (compacted) at a pressure of at least about 6500 psig and preferably at least 15000 psig (e.g., in a Chilsonator M-83 Compactor), crushed and screened. Other methods for preparing granules include, for instance, pelletization, extrusion, briquetting and the like; all of which are well known to the skilled artisan. Preferably, the granules are prepared by compaction.

The granules of this invention are preferably from about 4 mesh to about 60 mesh in size and more preferably from about 16 mesh to about 48 mesh in size.

As set forth above, when used in the concentrations recited herein, the ammonium sulfate imparts chemical stability to the insecticidal phosphoroamidothioate in the granular formulation. As used herein, the term "chemical stability" means that the amount of the insecticidal phosphoroamidothioate in the granular formulation does not diminish by more than about 10% when stored under accelerated storage conditions of 28 days at 55° C. as compared to the amount of the phosphoroamidothioate in the granulation formulation prior to storage. Under these accelerated conditions, insecticidal phosphoroamidothioate granules which do not result in diminished amounts of the phosphoroamidothioate under these accelerated conditions evidence the fact that such granules will possess excellent long term storage stability under ambient conditions. Without being limited to any theory, it is believed that phosphoroamidothioate are subject to hydrolysis in the granule which hydrolysis leads to inactive or less active components. It is also believed that this hydrolysis may be catalytically driven. It is further believed that in some way the use of a requisite amount of ammonium sulfate interferes with the degradation of the phosphoroamidothioate thereby imparting chemical stability to the granules.

While ammonium sulfate has heretofore been suggested in acephate pellets, the amount of ammonium sulfate required to impart chemical stability to phosphoroamidothioate granules is greater than that heretofore employed. That is to say that the present invention is an improvement over such previous uses of ammonium sulfate insofar as when used at the concentrations of this invention, the ammonium sulfate will provide for chemical stability to such granules. Accordingly, this effect is a concentration dependent effect achieved only by using a requisite concentration of ammonium sulfate which concentration is greater than that previously employed.

Once formulated, the granules are useful in a method for controlling insects by application of the granules onto the insecticidal habitat. In general, the granules are applied onto the habitat in an amount effective to be insecticidal to the insects. In a preferred embodiment, the granules are applied at a rate of at least about 0.5 lbs acephate per acre and more preferably at a rate of from about 0.5 lbs to about 2.0 lbs acephate per acre. Obviously, the amount of granules to be applied per acre will depend upon the concentration of acephate in the granules. Thus, for example, granules containing 10% acephate will need to be applied at 5 lbs per acre to achieve a dosage of 0.5 lbs acephate per acre The following examples illustrate certain embodiments of the invention but are not meant to limit the scope of the claims in any way.

EXAMPLES

Example 1

The purpose of this example is to demonstrate the criticality of employing at least 83 weight percent ammonium sulfate in the insecticidal phosphoroamidothioate granule in order to impart chemical stability to the granule.

Two different granular formulations containing acephate (Orthene ®) and ammonium sulfate were prepared and tested under accelerated storage conditions. Specifically, admixtures were prepared as follows:

|  | Weight Percent | |
|---|---|---|
|  | Formulation A | Formulation B |
| Orthene ® 90-S[1] | 11.1 | 11.1 |
| Cab-O-Sil M-5 | 0.5 | 0.5 |
| Corn Starch | — | 5.0 |
| Magnesium stearate | 0.5 | 0.5 |
| Ammonium Sulfate | 87.9 | 82.9 |

[1]Orthene ® 90-S contains 90% acephate.

The admixtures were then formulated into granules by first uniformily mixing the admixture. A requisite amount of the mixed admixture was then compacted into round tablets of approximately one square inch and ⅛ inch thickness. Tablets were then broken by hand and screened to granules of 20 to 50 mesh for us in stability studies.

The granules were analyzed for the amount of acephate by gas chromatography and then stored in sealed glass bottles maintained at 55° C. After storage for 10 and 28 days, the granules were again tested for acephate concentration. The results of these tests are as follows:

| Days in Storage | Amount of Acephate | | | |
|---|---|---|---|---|
| | Form. A | % Loss | Form. B | % Loss |
| 0 | 10.4 | — | 10.1 | — |
| 10 | 10.5 | — | 7.3 | 28 |
| 28 | 10.5 | — | 7.3 | 28 |

The above results demonstrate that when using less than about 83 weight percent ammonium sulfate, granules containing phosphoroamidothioates are not chemically stable to phosphoroamidothioate degradation whereas granules containing more than about 83 weight percent ammonium sulfate are chemically stable.

Example 2

The purpose of this example is to demonstrate the criticality of employing at least 83 weight percent ammonium sulfate in the insecticidal phosphoroamidothioate granule rather than at least 83 weight percent of a related sulfate salt, i.e., potassium sulfate.

Two different granular formulations containing acephate (Orthene ®) and either ammonium sulfate or potassium sulfate were prepared and tested under accelerated storage conditions. Specifically, admixtures were prepared as follows:

| | Weight Percent | |
|---|---|---|
| | Formulation A | Formulation B |
| Orthene ® 90-S | 11.1 | 11.1 |
| Cab-O-Sil M-5 | 0.5 | 0.5 |
| Magnesium stearate | 0.5 | 0.5 |
| Ammonium Sulfate | 87.9 | — |
| Potassium Sulfate | — | 87.9 |

The admixtures were then formulated into granules by first uniformily mixing the admixture. A requisite amount of the mixed admixture was then compacted into round tablets of approximately one square inch and ⅛ inch thickness. Tablets were then broken by hand and screened to granules of 20 to 50 mesh for use in stability studies.

The granules were analyzed for the amount of acephate by gas chromatography and then stored in sealed glass bottles maintained at 55° C. After storage for 10 and 28 days, the granules were again tested for acephate concentration. The results of these tests are as follows:

| Days in Storage | Amount of Acephate | | | |
|---|---|---|---|---|
| | Form. A | % Loss | Form. B | % Loss |
| 0 | 10.4 | — | 10.7 | — |
| 10 | 10.5 | — | 9.3 | 13 |
| 28 | 10.5 | — | 9.0 | 16 |

The above results demonstrate that when using at least about 83 weight percent of a sulfate salt other than ammonium sulfate, granules containing phosphoroamidothioates are not chemically stable to phosphoroamidothioate degradation.

Example 3

The purpose of this example is to demonstrate the criticality of employing at least 83 weight percent ammonium sulfate in the insecticidal phosphoroamidothioate granule rather than at least about 83 weight percent of a related ammonium salt, i.e., ammonium phosphate.

Two different granular formulations containing acephate (Orthene ®) and either ammonium sulfate or ammonium phosphate were prepared and tested under accelerated storage conditions. Specifically, admixtures were prepared as follows:

| | Weight Percent | |
|---|---|---|
| | Formulation A | Formulation B |
| Orthene ® 90-S | 11.1 | 11.1 |
| Cab-O-Sil M-5 | 0.5 | 0.5 |
| Magnesium stearate | 0.5 | 0.5 |
| Ammonium Sulfate | 87.9 | — |
| Ammonium Phosphate | — | 87.9 |

The admixtures were then formulated into granules by first uniformily mixing the admixture. A requisite amount of the mixed admixture was then compacted into round tablets of approximately one square inch and ⅛ inch thickness. Tablets were then broken by hand and screened to granules of 20 to 50 mesh for use in stability studies.

The granules were analyzed for the amount of acephate by gas chromatography and then stored in sealed glass bottles maintained at 55° C. After storage for 10 and 28 days, the granules were again tested for acephate concentration. The results of these tests are as follows:

| Days in Storage | Amount of Acephate | | | |
|---|---|---|---|---|
| | Form. A | % Loss | Form. B | % Loss |
| 0 | 10.4 | — | 10.4 | — |
| 10 | 10.5 | — | 8.5 | 18 |
| 28 | 10.5 | — | 0 | 100 |

The above results demonstrate that when using at least about 83 weight percent of an ammonium salt other than ammonium sulfate, granules containing phosphoroamidothioates are not chemically stable to phosphoroamidothioate degradation.

In view of the fact that the granules of this invention are chemically stable, use of these granules in methods for controlling insects will invariably lead to superior results as compared to granules heretofore used insofar as less amounts of the insecticidal phosphoroamidothioate will diminish over time.

From the foregoing description, various modifications and changes in the composition and method will occur to those skilled in the art. All such modifications coming within the scope of the appended claims are intended to be included therein.

What is claimed is:

1. A granular insecticidal composition comprising at least about 2 weight percent of an insecticidal compound or mixture of compounds of the formula:

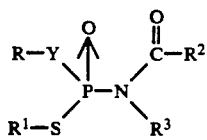

where R and $R^1$ individually are alkyl, alkenyl or alkynyl containing up to 6 carbon atoms, $R^2$ is hydrogen, alkyl containing 1 to 18 carbon atoms, cycloalkyl containing 3 to 8 carbon atoms, alkenyl containing 2 to 18 carbon atoms or alkynyl containing 3 to 18 carbon atoms, $R^3$ is hydrogen or alkyl containing 1 to 6 carbon atoms, and Y is oxygen or sulfur;

at least about 83 weight percent of ammonium sulfate; and one or more additives selected from the group consisting of:

(a) from about 0.5 to about 5 weight percent of a colloidal silica particle;

(b) from about 0.5 to about 5 weight percent of magnesium stearate; and (c) from about 1 to about 5 weight percent of corn starch, with the proviso that the total weight percent of additives (a), (b) and (c) in said composition ranges from at least 1 weight percent to less than 6 weight percent.

2. The composition of claim 1 wherein R and $R^1$ are independently methyl, ethyl, allyl or alkenyl; $R^2$ is H or alkyl; $R^3$ is hydrogen; and Y is oxygen.

3. The composition of claim 1 wherein R, $R^1$ and $R^2$ are methyl, $R^3$ is hydrogen and Y is oxygen.

4. A granular insecticidal composition comprising from about 2 to about 17 weight percent of an insecticidal compound or mixture of compounds of the formula:

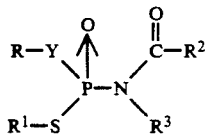

where R and $R^1$ individually are alkyl, alkenyl or alkynyl containing up to 6 carbon atoms, $R^2$ is hydrogen, alkyl containing 1 to 18 carbon atoms, cycloalkyl containing 3 to 8 carbon atoms, alkenyl containing 2 to 18 carbon atoms or alkynyl containing from 3 to 18 carbon atoms, $R^3$ is hydrogen or alkyl containing 1 to 6 carbon atoms, and Y is oxygen or sulfur;

from about 83 to about 98 weight percent of ammonium sulfate; and one or more additives selected from the group consisting of:

(a) from about 0.5 to about 5 weight percent of a colloidal silica particle;

(b) from about 0.5 to about 5 weight percent of magnesium stearate; and (c) from about 1 to about 5 weight percent of corn starch, with the proviso that the total weight percent of additives (a), (b) and (c) in said composition ranges from at least 1 weight percent to less than 6 percent.

5. The composition of claim 4 wherein the granular composition comprises about 15 weight percent of the insecticidal compound or mixture of compounds and about 85 weight percent ammonium sulfate.

6. The composition of claim 4 wherein R and $R^1$ are independently methyl, ethyl, allyl or alkenyl; $R^2$ is H or alkyl; $R^3$ is hydrogen; and Y is oxygen.

7. The composition of claim 4 wherein R, $R^1$ and $R^2$ are methyl, $R^3$ is hydrogen and Y is oxygen.

8. The composition of claim 1 wherein the granular composition is prepared by compaction.

9. A method for killing insects which comprises contacting insects or their growth habitats with an insecticidally effective amount of granules comprising at least about 2 weight percent of a compound or a mixture of compounds of the formula:

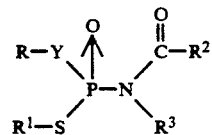

where R and $R^1$ individually are alkyl, alkenyl or alkynyl containing up to 6 carbon atoms, $R^2$ is hydrogen, alkyl containing 1 to 18 carbon atoms, cycloalkyl containing 3 to 8 carbon atoms, alkenyl containing 2 to 18 carbon atoms or alkynyl containing 3 to 18 carbon atoms, $R^3$ is hydrogen or alkyl containing 1 to 6 carbon atoms, and Y is oxygen or sulfur;

at least about 83 weight percent of ammonium sulfate; and one or more additives selected from the group consisting of:

(a) from about 0.5 to about 5 weight percent of a colloidal silica particle;

(b) from about 0.5 to about 5 weight percent of magnesium stearate; and (c) from about 1 to about 5 weight percent of corn starch, with the proviso that the total weight percent of additives (a), (b) and (c) in said composition ranges from at least 1 weight percent to less than 6 weight percent.

10. The method of claim 9 wherein R and $R^1$ are independently methyl, ethyl, allyl or alkenyl; $R^2$ is H or alkyl; $R^3$ is hydrogen; and Y is oxygen.

11. The method of claim 10 wherein R, $R^1$ and $R^2$ are methyl, $R^3$ is hydrogen and Y is oxygen.

12. A method for killing insects which comprises contact insects or their growth habitats with an insecticidally effective amount of granules comprising from about 2 to about 17 weight percent of a compound or a mixture of compounds of the formula:

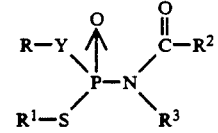

where R and $R^1$ individually are alkyl, alkenyl or alkynyl containing up to 6 carbon atoms, $R^2$ is hydrogen, alkyl containing 1 to 18 carbon atoms, cycloalkyl containing 3 to 8 carbon atoms, alkenyl containing 2 to 18 carbon atoms or alkylnyl containing 3 to 18 carbon atoms, $R^3$ is hydrogen or alkyl containing 1 to 6 carbon atoms, and Y is oxygen or sulfur;

from about 83 to about 98 weight percent of ammonium sulfate; and one or more additives selected from the group consisting of:

(a) from about 0.5 to about 5 weight percent of a colloidal silica particle;

(b) from about 0.5 to about 5 weight percent of magnesium stearate; and (c) from about 1 to about 5 weight percent of corn starch, with the proviso that the total weight percent of additives (a), (b) and (c) in said composition ranges from at least 1 weight percent to less than 6 weight percent.

13. The method of claim 12 wherein the granular composition comprises about 15 weight percent of the insecticidal compound or mixtures of compounds and about 85 weight percent ammonium sulfate.

14. The method of claim 12 wherein R and $R^1$ are independently methyl, ethyl, allyl or alkenyl; $R^2$ is H or alkyl; $R^3$ is hydrogen; and Y is oxygen.

15. The method of claim 12 wherein R, $R^1$ and $R^2$ are methyl, $R^3$ is hydrogen and Y is oxygen.

16. The method of claim 12 wherein the granular composition is prepared by compaction.

17. A method for killing insects which comprises contacting plants which are ingested by said insects or the plant's growth medium with a granular composition comprising at least about 2 weight percent of a compound or a mixture of compounds of the formula:

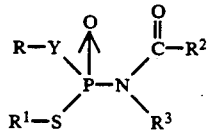

where R and $R^1$ individually are alkyl, alkenyl or alkynyl containing up to 6 carbon atoms, $R^2$ is hydrogen, alkyl containing 1 to 18 carbon atoms, cycloalkyl containing 3 to 8 carbon atoms, alkenyl containing 2 to 18 carbon atoms or alkynyl containing 3 to 18 carbon atoms, $R^3$ is hydrogen or alkyl containing 1 to 6 carbon atoms, and Y is oxygen or sulfur;

at least about 83 weight percent of ammonium sulfate; and one or more additives selected from the group consisting of:

(a) from about 0.5 to about 5 weight percent of a colloidal silica particle;

(b) from about 0.5 to about 5 weight percent of magnesium stearate; and (c) from about 1 to about 5 weight percent of corn starch, with the proviso that the total weight of additives (a), (b) and (c) in said composition ranges from at least 1 weight percent to less than 6 weight percent.

18. A granular insecticidal composition comprising at least about 2 weight percent of an insecticidal compound or mixture of compounds of the formula:

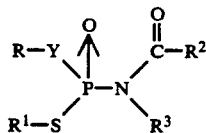

where R and $R^1$ individually are alkyl, alkenyl or alkynyl containing up to 6 carbon atoms, $R^2$ is hydrogen, alkyl containing 1 to 18 carbon atoms, cycloalkyl containing 3 to 8 carbon atoms, alkenyl containing 2 to 18 carbon atoms or alkynyl containing 3 to 18 carbon atoms, $R^3$ is hydrogen or alkyl containing 1 to 6 carbon atoms, and Y is oxygen or sulfur;

at least about 83 weight percent of ammonium sulfate; and one or more additives selected from the group consisting of:

(a) from about 0.5 to about 5 weight percent of a colloidal silica particle;

(b) from about 0.5 to about 5 weight percent of magnesium stearate;

(c) from about 1 to about 5 weight percent of corn starch;

(d) from about 0.2 to about 5 weight percent of surfactant; and (e) from about 0.05 to about 2 weight percent of deodorant, with the proviso that the total weight percent of additives (a), (b), (c), (d), and (e) in said composition ranges from at least 1 weight percent to less than 6 weight percent.

19. A granular insecticidal composition according to claim 1, wherein the composition consists essentially of said insecticidal compound or mixture of compounds, said ammonium sulfate, and said one or more additives.

20. A granular insecticidal composition according to claim 19, wherein the composition is prepared by compaction and does not contain any binders.

* * * * *